(12) United States Patent
Liu

(10) Patent No.: US 7,287,699 B2
(45) Date of Patent: Oct. 30, 2007

(54) SENSOR CALIBRATION METHOD AND SYSTEMS

(75) Inventor: James Z T Liu, Belvidere, IL (US)

(73) Assignee: Honeywell International Inc., Morristown, NJ (US)

( * ) Notice: Subject to any disclaimer, the term of this patent is extended or adjusted under 35 U.S.C. 154(b) by 238 days.

(21) Appl. No.: 11/199,091

(22) Filed: Aug. 5, 2005

(65) Prior Publication Data

US 2007/0029388 A1 Feb. 8, 2007

(51) Int. Cl.
G06F 17/00 (2006.01)

(52) U.S. Cl. ............ 235/462.15; 235/375; 235/462.01; 235/487; 235/494

(58) Field of Classification Search ........... 235/462.15, 235/474, 476, 495; 702/91
See application file for complete search history.

(56) References Cited

U.S. PATENT DOCUMENTS

| | | | | |
|---|---|---|---|---|
| 4,745,269 A * | 5/1988 | Van Gils | .................. | 235/487 |
| 5,422,469 A | 6/1995 | Bard et al. | .................. | 235/462 |
| 5,471,043 A | 11/1995 | Knapp et al. | ............... | 235/472 |
| 5,521,367 A | 5/1996 | Bard et al. | .................. | 235/462 |
| 5,705,799 A | 1/1998 | Li | ............................. | 235/462 |
| 6,195,053 B1 | 2/2001 | Kodukula et al. | .......... | 343/702 |
| 6,196,070 B1 | 3/2001 | Piascik et al. | ............ | 73/861.74 |
| 6,587,980 B2 | 7/2003 | Debenham | ................... | 714/724 |
| 6,588,670 B2 * | 7/2003 | Bukowski | .............. | 235/462.45 |
| 6,778,928 B2 | 8/2004 | Stiller | ........................ | 702/104 |
| 6,826,966 B1 | 12/2004 | Karbassi et al. | ......... | 73/861.52 |
| 6,866,199 B1 * | 3/2005 | Keech et al. | ................ | 235/490 |
| 6,871,537 B1 | 3/2005 | Gehman et al. | .......... | 73/204.26 |
| 6,907,787 B2 | 6/2005 | Cook et al. | ................... | 73/700 |

FOREIGN PATENT DOCUMENTS

EP 1152597 A2 * 11/2001

* cited by examiner

*Primary Examiner*—Seung Ho Lee
(74) *Attorney, Agent, or Firm*—Kermit D. Lopez; Luis M. Ortiz

(57) ABSTRACT

A sensor calibration system includes a sensor having one or more sensing components formed on a substrate. A barcode can also be configured or printed from or on the, such that the barcode contains calibration data associated with a calibration of the sensor and the sensing component(s). One or more barcode readers can be provided which can scan the barcode and reads the calibration data associated with the calibration of the sensor and the sensing components thereof, in order to reduce the need for trimming the sensor while also providing for a reduction in associated manufacturing and production costs. A binning methodology can also be implemented for reducing overall sensor manufacturing costs.

16 Claims, 2 Drawing Sheets

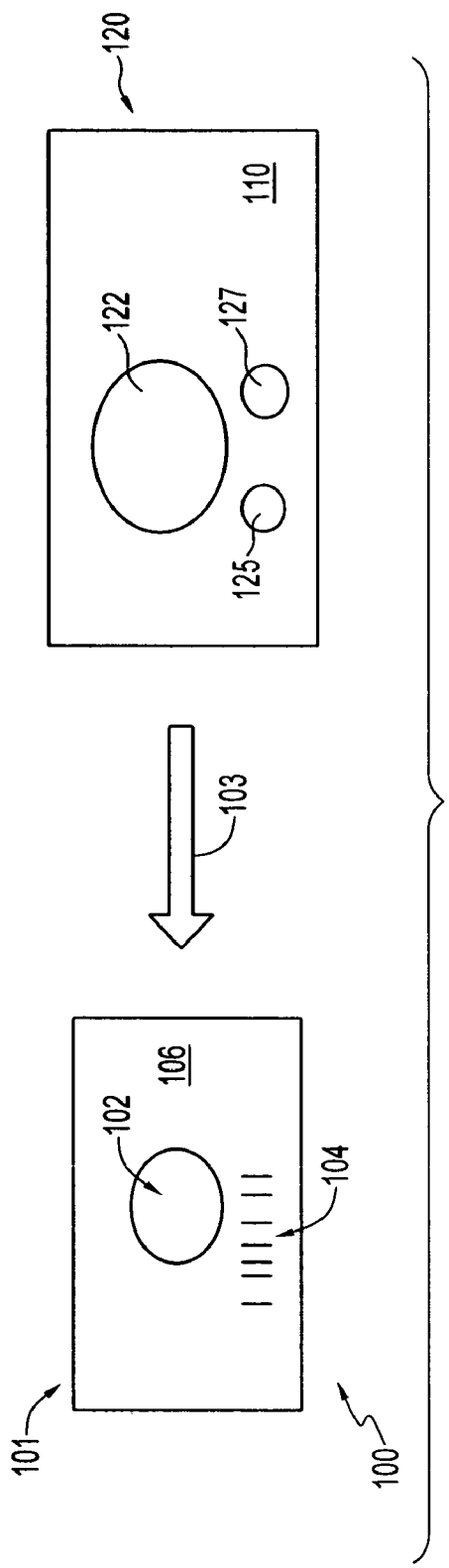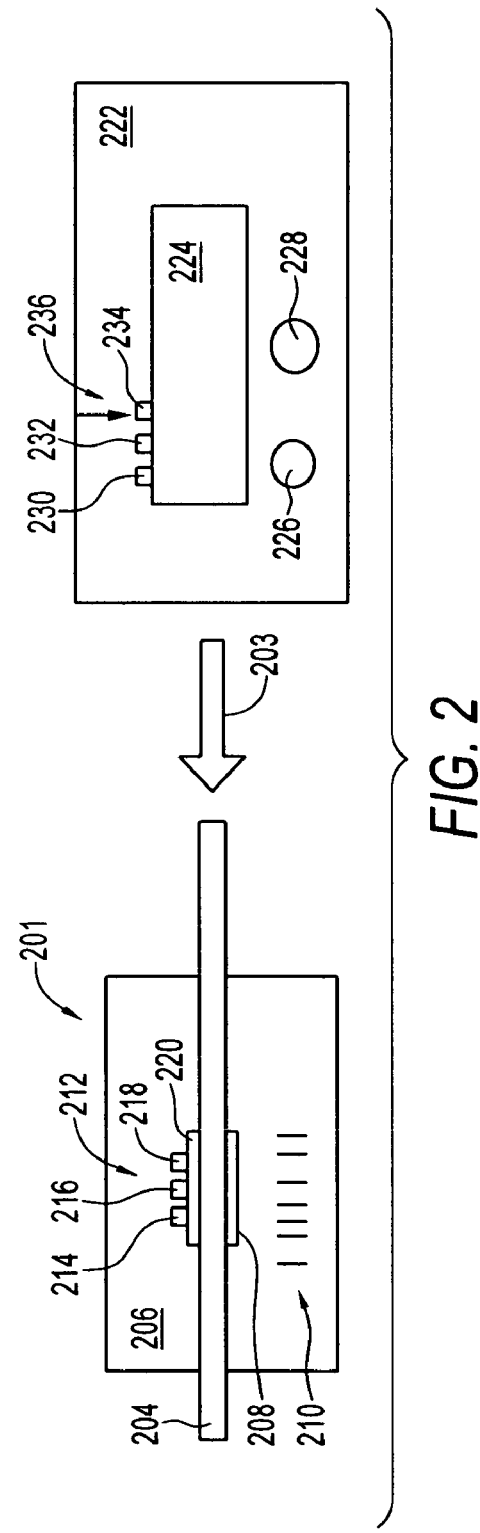

SENSOR CALIBRATION METHOD AND SYSTEMS

TECHNICAL FIELD

Embodiments are generally related to sensing devices and components thereof. Embodiments are also related to sensor calibration methods and systems. Embodiments are additionally related to barcode and barcode reader devices and methodologies. Embodiments additionally relate to manufacturing and production binning techniques.

BACKGROUND OF THE INVENTION

Electronic sensors are employed in a number of different fields of technology. Such sensors may be employed to detect changes in environmental parameters, such as atmospheric pressure, or may be employed to detect changes in forces applied to the object to which they are attached, for example.

One type of sensor that is often utilized in sensor applications is the "flow sensor". An example of a flow sensor is disclosed in U.S. Pat. No. 6,871,537, entitled "Liquid Flow Sensor Thermal Interface Methods and Systems", which issue to Richard W. Gehman, et al. on Mar. 29, 2005 and is assigned to Honeywell International Inc. of Morristown, N.J., U.S.A. U.S. Pat. No. 6,871,537, which is incorporated herein by reference that measures the thermal conductivity of a fluid. The sensor disclosed in U.S. Pat. No. 6,871,537 is configured to comprise one or more sensing element associated with a sensor substrate. A heater is generally associated with said sensor wherein said heater provides heat to said fluid. A film component is also provided that isolates said fluid from said heater and said sensor, such that said film component conducts heat in a direction from said heater to said sensor, thereby forming a thermal coupling between said sensor, said heater and said fluid, which permits said sensor to determine a composition of said fluid by measuring thermal conductivity thereof without undesired losses of heat in other directions. The film component can be configured on or in the shape of a tubing or a flow channel.

Other types of sensors include "temperature sensors" and "pressure sensors". An example a pressure and/or temperature sensor is disclosed in U.S. Pat. No. 6,907,787, entitled "Surface Acoustic Wave Pressure Sensor with Microstructure Sensing Elements," which issued to James Cook, et al. on Jun. 21, 2005 and is assigned to Honeywell International Inc. of Morristown, N.J., U.S.A. U.S. Pat. No. 6,907,787, which is incorporated herein by reference in its entirety, generally discloses a pressure and temperature sensor system, comprising one or more microstructure temperature-sensing elements formed on a substrate within a hermetically sealed area thereof, wherein such microstructure temperature-sensing elements comprise (Surface Acoustic Wave) SAW temperature-sensing elements. Additionally, one or more microstructure pressure-sensing elements can be located above a sensor diaphragm on the substrate, such that the microstructure pressure-sensing element is formed from a SAW pressure-sensing element. One or more contacts can also be provided, which assist in maintaining the hermetically sealed area and which protrude through the substrate for support and electrical interconnection of the pressure and temperature sensor system.

For satisfactory functioning of a sensor, regardless of the type of sensor utilized, prior calibration of the sensor system or the individual sensors is preferably accomplished in principle for the subsequent accurate measurement of environmental parameters. Calibration can be accomplished in a laboratory-like environment either before or after deployment of the sensors. The various calibration methods usually require controlled movement of the sensors or the objects or environmental conditions detected by the sensor systems. Often it is even desirable to detect a particular parameter, which is then referred to as a calibration field accordingly. To guarantee permanent functional reliability, subsequent repeated checking of the calibration for possible changes is desirable, which may be very complicated.

Sensors of extremely low-cost are typically based on sophisticated but extremely compact components and require new methods of calibration. Traditional sensors are calibrated by laser-trimming of resistors, capacitors, inductors and/or other necessary sensor components. Trimming in this manner, however, increases the overall cost of sensor, and in some cases, may introduce drift due to the heat from laser. RFID provides another technique for calibration and data storage, but in extremely low cost sensor designs, even, for example, 5-10 cents RFID components contribute a great deal to the overall sensor costs.

In manufacturing processes for sensor devices, particularly those, which incorporate substrate and die processing, numerous expensive and time-consuming steps are involved in producing such sensor device assemblies. These steps may include the following: (1) forming a dice on a sensor substrate, (2) testing the dice, (3) cutting dice from the substrate, (4) connecting a die or dice to a lead frame, (5) encapsulating the die or dice, lead frame, connecting wires, and any auxiliary circuitry, (6) performing burn-in and/or providing other stresses to the dice, and (7) testing the sensor device assembly at various stages of processing.

In sensor manufacturing, typically, the term "front-end" refers to the fabrication of sensor devices to the level of completed and tested components. The term "backend" refers to production stages of sensor devices occurring after the front-end and including such sensor device production stages as packaging, burn-in, testing, sorting, marking, and environmental testing.

When tested, a sensor device may have some failure due to various causes including, but not limited to, an internal defect in the die or chip, a bad bonding connection, or a bad connection between a lead finger and a probe or other test device. Failures in a completed sensor device assembly can prevent it from operating as intended. In spite of painstaking attention to detail, failures may be introduced at various levels of production. For example, defects in forming the die or substrate may cause a failure. It has been found, however, that some defects are manifest immediately, while other defects are manifest only after the die has been operated for some period of time.

It is therefore believed that a need exists for reducing sensor production costs by implementing improved calibration methodologies and systems, and also providing for improved sensor manufacturing and binning processes. Such improvements are therefore disclosed herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensor calibration system.

It is another aspect of the present invention to provide for a sensor calibration system that incorporates the use of barcode and barcode reader devices and methodologies.

It is also an aspect of the present invention to provide for an improved manufacturing and production method for binning inexpensive sensors in order to maintain low-cost manufacturing processes thereof.

The aforementioned aspects and other objectives and advantages can now be achieved as described herein. A sensor calibration system is disclosed, which includes a sensor having one or more sensing components formed on a substrate. A barcode can also be configured or printed from or on the, such that the barcode contains calibration data associated with a calibration of the sensor and the sensing component(s). One or more barcode readers can be provided which can scan the barcode and reads the calibration data associated with the calibration of the sensor and the sensing components thereof, in order to reduce the need for trimming the sensor while also providing for a reduction in associated manufacturing and production costs.

The sensing components associated with the sensor can be, implemented as, for example, a sensor diaphragm. The sensor can be implemented as, for example, a pressure sensor or a flow sensor. Such a flow sensor can be associated with a flow tube for sensing flow data associated with a flow of fluid or gas through the flow tube. A wireless sensor reading unit can also be provided which scans and reads the calibration data from the barcode in association with the barcode readers. Such a wireless sensor reading unit can be implemented as an inductively coupled reader, an optical reader, a passive acoustic reader or a combination thereof. The barcode readers are preferably implemented as optical barcode readers.

Additionally, a binning method for sensor production is disclosed herein. In general, plurality of sensors can be produced during a manufacturing production process, wherein the are produced without trimming in a variation range of a particular percentage comprising A %. At least one test of at least one sensor can be performed among the plurality of sensors for identifying one or more sensor types. The sensors can then be automatically binned into a particular number of groups represented by a variable n. Thereafter, the sensors can be automatically grouped into the particular number of groups based on an application requiring an error of A/n %, thereby reducing production costs associated with manufacturing the plurality of sensors.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 1 illustrates a wireless pressure sensor calibration and data storage system, which can be implemented in accordance with a preferred embodiment;

FIG. 2 illustrates a disposable flow sensor calibration and data storage system, which can be implemented in accordance with an alternative embodiment.

DETAILED DESCRIPTION

Figure 3:
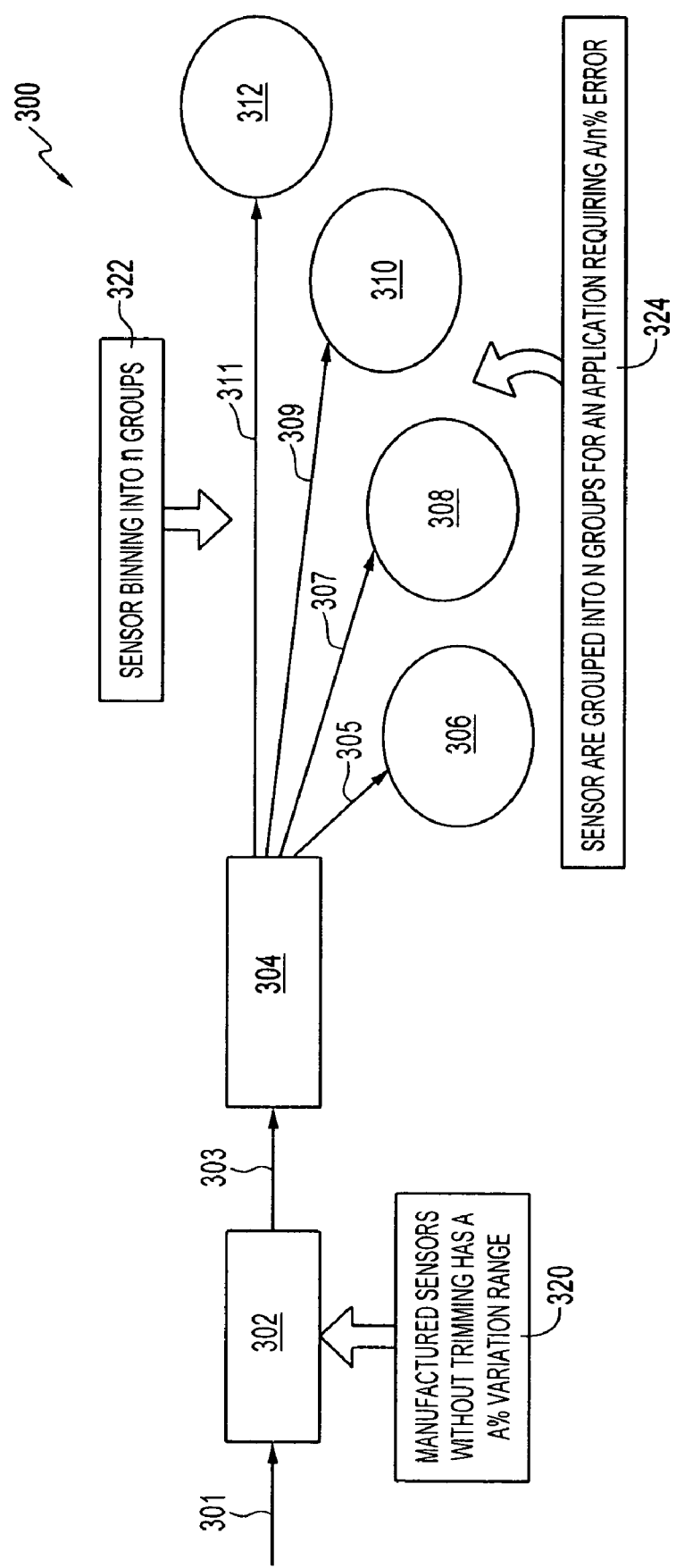
FIG. 3 illustrates a flow chart of operations depicting logical operation steps for implementing a sensor binning process, in accordance with a preferred embodiment.

The particular values and configurations discussed in these non-limiting examples can be varied and are cited merely to illustrate at least one embodiment and are not intended to limit the scope thereof.

FIG. 1 illustrates a wireless pressure sensor calibration and data storage system 100, which can be implemented in accordance with a preferred embodiment. System 100 includes a wireless pressure sensor 101 that includes a substrate 106 and a pressure sensor diaphragm 102 formed thereon or from substrate 106. The wireless pressure sensor 101 further includes a barcode 104 printed on one side or the "sensor side" of the wireless pressure sensor 101. The barcode 104 can be printed directly on the substrate 106.

The barcode 104 stores sensor calibration information associated with sensor 101. The barcode 104 is utilized as a calibration data storage mechanism. System 100 further includes a pressure reader 110 composed of a wireless pressure reading unit 122 and one or more optical barcode readers 125, 127. The wireless pressure reading unit 122 functions as a mechanism that can be implemented as, for example, an inductively coupled reader, an optical reader or a passive acoustic reader. Calibration curves and/or calibration data is stored in the barcode 104. The substrate 106 can be implemented as any number of substrate materials, such as, for example, a PCB (Printed Circuit Board), silicon, glass, plastic, or a combination thereof.

Barcode 104 comprises an array of machine-readable rectangular bars and spaces arranged in a specific manner defined in international standards to represent data, including, for example, letters, numbers, and other human-readable symbols. Optical barcode readers 125, 127 can be implemented, for example, as laser-optical readers that scan barcode 104 and then utilize logic to translate from a scanned barcode to a human-readable representation, such as, for example human-readable sensor calibration data. Barcode readers 125, 127 can also be implemented in the context of a light source, a lens and a photo conductor that translates optical impulses into electrical signals. Additionally, barcode readers 125, 127 can contain decoder circuitry (not shown in FIG. 1) that analyzes image data provided barcode 104. Note that in FIG. 1 the actual barcode reading process is illustrated graphically by arrow 103.

FIG. 2 illustrates a disposable flow sensor calibration and data storage system 200, which can be implemented in accordance with an alternative embodiment. Note that FIG. 2 illustrates variations to the sensor system 100 depicted in FIG. 1. The disposable flow sensor calibration and data storage system 200 includes a disposable flow sensor 201 that includes a sensor substrate 206 associated with a flow tube 204. A flow sensor die portion 208 is located adjacent to or integrated with the flow tube 204, depending upon design considerations. A flow sensor die portion 220 is also associated with the flow tube 204 and may actually form part of the flow sensor die portion 208, again depending upon design considerations. That is, the flow sensor die portion 220 and flow sensor die portion 208 may constitute the same flow sensor die.

A group 212 of wired connections 214, 216, and 218 are generally connected to the flow sensor die portion 220. Assuming that the flow sensor die portion 220 and the flow sensor die portion 208 are implemented in the context of a single flow sensor die, then the group 212 of wired connections 214, 216, and 218 can also communicate electrically with both die portions 220 and 208. The disposable flow sensor calibration and data storage system 200 further incorporates the use of barcode 210 printed on one side or the "sensor side" of the disposable flow sensor 201. The barcode 210 can be implemented as an array of machine-readable rectangular bars and spaces arranged in a specific manner defined in international standards to represent data, including, for example, letters, numbers, and other human-readable symbols. The substrate 206 can be implemented as any number of substrate materials, such as, for example, a PCB (Printed Circuit Board), silicon, glass, plastic, or a combination thereof.

The disposable flow sensor calibration and data storage system 200 further includes the use of a flower sensor reader 222, which can be configured to include a wired flow sensor reading unit 224, the mechanism of which can be based on thermally conductivity type readers or flow induced stress measurement devices, again, depending upon design considerations. A group 236 of wired connections 230, 234, 234 can be connected and/or integrated with the wired flow sensor reading unit 224. Note that in FIG. 2 the actual barcode reading process is illustrated graphically by arrow 203.

The disposable flow sensor calibration and data storage system 200 additionally includes optical barcode readers 226, 228, which are similar to the optical barcode readers 125, 127 depicted in FIG. 1. That is, the optical barcode readers 226, 228 can be implemented, for example, as laser-optical readers that scan barcode 210 and then utilize logic to translate from a scanned barcode to a human-readable representation, such as, for example human-readable sensor calibration data. Barcode readers 226, 228 can also be implemented in the context of a light source, a lens and a photo conductor that translates optical impulses into electrical signals. Additionally, barcode readers 226, 228 can contain decoder circuitry (not shown in FIG. 2) that analyzes image data provided barcode 210. Barcode readers 226, 228 can constitute a combination of a barcode scanner and its associated decoder. The scanner is a device that produces a signal representing the bars and spaces of a barcode. The decoder converts that symbol so a computer can understand it. Together the barcode scanner and decoder produce a barcode reader.

In general, the barcode readers 125, 127 and 226, 228 can be based on any number of various optical readers and scanning systems for reading barcode symbols such as barcodes 104 and 210 that on a label or the surface of an article such as respective substrates 106 and 206. The barcode symbol itself implemented via barcodes 104 and 210 can constitute a coded pattern of indicia comprised of a series of bars of various widths spaced apart from one another to bound spaces of various widths, the bars and spaces having different light-reflecting characteristics. The readers 125, 127 and 226, 228 and associated scanning systems can electro-optically transform the graphic indicia into electrical signals, which are decoded into alpha-numerical characters intended to be descriptive of the article or some characteristic of it, such as, for example, calibration data associated sensors 101 and 201. Such characters can be represented in digital form, and utilized as an input to a data processing system (not show in FIGS. 1-2) for sensor calibration applications.

The systems 100, 200 respectively depicted in FIGS. 1-2, represent examples of sensor systems that can be effectively implemented in the context of low-cost sensor applications. In low-cost or disposable pressure sensor designs such as the pressure sensor 101 depicted in FIG. 1 or the low-cost flow sensor 201 depicted in FIG. 1, respective barcodes 104 and 210 can be utilized as the calibration storage mechanism. In such designs, a user may pay more on the re-usable interrogation or electronics, Under such circumstances, however, the sensors 101, 201 do not have to be trimmed, because the calibration curves and/or other calibration data is stored directly on the barcodes 104, 210. This saves costs in the long run, because traditional calibration mechanisms and methodologies are much more expensive, unlike the calibration procedure and system discussed herein. For example, in a wireless pressure sensor design, such as that depicted in FIG. 1, the pressure can be read through an LC tank and the pressure results read inductively. While the calibration curves are printed near each sensor. In a wire disposable pressure sensor design, the pressure an be read using a capacitive or piezoresistive principles. Alternatively, both the pressure and calibration data can be read optically.

FIG. 3 illustrates a flow chart of operations depicting logical operation steps for implementing a sensor binning process 300, in accordance with a preferred embodiment. As indicated previously, sensors manufactured in a low-cost production environment can lose tolerance materials and often result in widely variable and unreliable production processes. Such sensors could be trimmed during sensor calibration operations, but the trimming elements and associated components (e.g., trim resistor, capacitor, inductor, etc.), however, contribute to a large percentage of the total cost of the "low cost" sensor design. For example, a trim capacitor may cost from 8 to 27 cents, while a low cost pressure sensor cost target may be approximately 20 cents.

Without a trimming process, such sensors can be binned into different groups during the calibration process. For example, if the sensors possess a 30% variation range, they can be binned into 3 groups of, for example, −15% to 5%, −5% to 5%, and 5% to 15%, for a 10% application. In a medical application scenario, for example, three binned group (e.g., colored or numbered) can be used in three different locations (e.g., arterial line, after blood out of patient, before blood pump, dialyses line, after blood pump, before dialyses, venous, line after dialyses, before patient, etc.). Usually there is one factor that dominates variations in the sensor. Such a factor can be determined through prudent design considerations among factors including cost of materials and processes, and variations included to the sensor by each material/process. Such "three groups" of sensors can be separated based on such a dominant factor (e.g., the pressure diaphragm thickness variation). Within each group, sensors can generate a similar response.

In general terms, the sensors can be thought of as possessing an A % variation range and can thus be binned into particular groups (e.g., −A/2% to −(A/2−A/n) %; −(A/2−A/n) % to −(A/d−2A/n) % . . . (A/2−A/n) % to A/2%) for an application allowing for an error of A/n %. The "n" binned group (colored or numbered) will always be used in "n" different locations for "n" different customers.

Thus, as indicated at arrow 301, the initial sensor binning process begins. As indicated next at block 302, sensor manufacturing occurs. Manufactured sensors without trimming possess an A % variation range as indicated at block 320, which is associated with the manufacturing process illustrated by block 302. As indicated thereafter by arrow 303, the process continues. Next, as depicted at block 304, sensor testing occurs. Next, sensor binning into "n" groups occurs, as indicated at by arrows 305, 307, 309, and 311. Block 322 indicates binning into the "n" groups. The sensors can be grouped into "n" groups for an application requiring an A/n % errors, as respectively depicted by blocks 306, 308, 310, and 312. Block 324 generally describes the action of grouping that occurs with respect to blocks 306, 308, 310, 312, which are represented in FIG. 3 as circles or ovals.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A sensor calibration system, comprising:
   a sensor having at least one sensing component formed on a substrate; a barcode formed on said substrate, wherein said barcode contains calibration data associated with a calibration of said sensor and said at least one sensing component; and
   at least one barcode reader, which scans said barcode and reads said calibration data associated with said calibration of said sensor and said at least one sensing component thereof, in order to reduce a need for trimming said sensor and reduce production costs thereof.

2. The system of claim 1 wherein said at least one sensing component comprises a sensor diaphragm.

3. The system of claim 2 wherein said sensor diaphragm comprises a pressure sensing diaphragm.

4. The system of claim 1 wherein said sensor comprises a pressure sensor.

5. The system of claim 1 wherein said sensor comprises a flow sensor associated with a flow tube for sensing flow data associated with a flow of fluid or gas through said flow tube.

6. The system of claim 1 further comprising a wireless sensor reading unit that scans and reads said calibration data from said barcode in association with said at least one barcode reader.

7. The system of claim 1 wherein said wireless sensor reading unit comprises an inductively coupled reader.

8. The system of claim 1 wherein said wireless sensor reading unit comprises an optical reader.

9. The system of claim 1 wherein said wireless sensor reading unit comprises a passive acoustic reader.

10. The system of claim 1 wherein said at least one barcode reader comprises an optical reader.

11. A sensor calibration system, comprising:
    a sensor having at least one sensing component formed on a substrate, wherein said at least one sensing component comprises a sensor diaphragm;
    a barcode formed on said substrate, wherein said barcode contains calibration data associated with a calibration of said sensor and said at least one sensing component;
    at least one barcode reader, which scans said barcode and reads said calibration data associated with said calibration of said sensor and said at least one sensing component thereof, in order to reduce a need for trimming said sensor and reduce production costs thereof; and
    a wireless sensor reading unit that scans and reads said calibration data from said barcode in association with said at least one barcode reader.

12. The system of claim 11 wherein said wireless sensor reading unit comprises an inductively coupled reader.

13. The system of claim 11 wherein said wireless sensor reading unit comprises an optical reader.

14. The system of claim 11 wherein said wireless sensor reading unit comprises a passive acoustic reader.

15. The system of claim 11 wherein said at least one barcode reader comprises an optical reader.

16. The system of claim 11 wherein said wireless sensor reading unit comprises at least one of the following types of readers: an inductively coupled reader, an optical reader, or a passive acoustic reader.

* * * * *